United States Patent [19]

Nitsch

[11] Patent Number: 5,561,226

[45] Date of Patent: Oct. 1, 1996

[54] PROCESS FOR THE PRODUCTION OF A PYROGEN-FREE FRUCTAN WHICH IS READILY WATER-SOLUBLE

[75] Inventor: Ernst Nitsch, Linz, Austria

[73] Assignee: Laevosan Gesellschaft mbH, Linz, Austria

[21] Appl. No.: 94,152

[22] PCT Filed: Jan. 21, 1992

[86] PCT No.: PCT/EP92/00120

§ 371 Date: Nov. 15, 1993

§ 102(e) Date: Nov. 15, 1993

[87] PCT Pub. No.: WO92/13005

PCT Pub. Date: Aug. 6, 1992

[30] Foreign Application Priority Data

Jan. 23, 1991 [DE] Germany ............... 41 01 910.5

[51] Int. Cl.$^6$ ............... C07H 1/06; C07H 1/08; A61K 35/78
[52] U.S. Cl. ............... 536/128; 424/195.1; 536/123.1
[58] Field of Search ............... 514/56, 54; 424/195.1, 424/180; 536/123.1, 128

[56] References Cited

U.S. PATENT DOCUMENTS

| | | | |
|---|---|---|---|
| 3,893,995 | 7/1975 | Nitsch et al. ............... | 260/209 R |
| 4,198,401 | 4/1980 | Pegel ............... | 424/195 |
| 4,421,852 | 12/1983 | Hoehn et al. ............... | 435/99 |
| 4,877,777 | 10/1989 | DiLuzio ............... | 514/54 |
| 4,900,722 | 2/1990 | Williams et al. ............... | 514/54 |
| 5,051,408 | 9/1991 | Cooper ............... | 514/54 |

FOREIGN PATENT DOCUMENTS

| | | |
|---|---|---|
| 0478837 | 10/1990 | European Pat. Off. . |
| 2158467 | 6/1972 | Germany . |
| 60-160893 | 8/1985 | Japan . |

OTHER PUBLICATIONS

Estelberger et al. *Eur. J. Clin. Chem. Clin Biochem.*, vol. 33(4), 201–209, (1995) [Abstract Only].

Nitsch et al. *Carbohydrate Research*, vol. 72, pp. 1–12, (1979). [Abstract Only].

*Primary Examiner*—John Kight
*Assistant Examiner*—Howard C. Lee
*Attorney, Agent, or Firm*—Felfe & Lynch

[57] ABSTRACT

A process is described for the production of a readily water-soluble fructan as well as a well-tolerated renal diagnostic agent containing such a fructan. In the process an aqueous fructan extract obtained from parts of plants is ultrafiltered over a first membrane which retains carbohydrates and proteins with a higher molecular weight but which allows passage of fructan and the filtrate obtained in this way is then filtered in a second ultrafiltration through a membrane which retains fructan but which allows passage of salts and low-molecular substances such as monosaccharides and oligosaccharides. The fructan obtained in this way is used as a renal diagnostic agent together with physiologically tolerated buffer substances at an osmolality which corresponds to that of blood and which has a pH of 5.0 to 7.0.

8 Claims, No Drawings

PROCESS FOR THE PRODUCTION OF A PYROGEN-FREE FRUCTAN WHICH IS READILY WATER-SOLUBLE

DESCRIPTION

The present invention concerns a process for the production of a pyrogen-free fructan which is readily water-soluble as well as a renal diagnostic agent based on such a fructan that can be applied parenterally.

Fructans, also called polyfructosans, are oligosaccharides and polysaccharides which are constructed of straight or branched fructose chains grafted onto a sucrose parent molecule. Substantial differences can occur in their physical properties depending on the degree of branching and polymerisation such as e.g. solubility in water. Many fructans are stored in plants as reserve carbohydrates and occur predominantly in subterranean parts of Compositae, Campanulaceae, grasses and Liliaceae.

A particular application of fructans is in renal diagnostics especially for the determination of the glomerular filtration rate. Inulin, a fructan from the roots of various species of Compositae such as chicory, dahlias and topinambur, is usually used as the standard test, substance for this (A. N. Richard, B. B. Westfall, P. A. Bott: Proc. Soc. Exp. Biol., N.Y. 32 (1934), 73 and O. Schück: Examination of Kidney Function, Martinus Nijnhoff Publishers, Boston 1984, p. 9 ff). Inulin has the advantage that after parenteral application it is neither changed by metabolism nor is it stored in the organism but is filtered by the renal glomeruli and is not reabsorbed in the tubuli (J. A. Shannon, H. W. Smith: J. Clin. Inv. 14 (1935), 393). However, for everyday clinical routine inulin has the disadvantage that it is only very sparingly soluble in water and thus aqueous preparations crystallize during storage and have to be dissolved again by prolonged heating before application. However, during this process depending on the duration of heat exposure inulin is attacked hydrolytically and may be degraded to fructose. A further disadvantage is that if the dissolution is incomplete remnants of undissolved inulin particles remain in the preparation which are not easily detectable and can cause severe circulatory complications after injection. Thus, in the Austrian Patent specification 304769 it is proposed that other water-soluble fructans, namely from the storage organs of plants from the Liliaceae, Amaryllidaceae and Gramineae families such as sinistrin and phlein should be used as a substitute for inulin. Like inulin these are composed of ca. 10 to 40 fructose units corresponding to molecular weights of ca. 1600 to 6500.

In the older literature, O. Schmiedeberg: Hoppe Seyler's Z. Physiol. Chem. 3 (1979), 112 and G. Klein: "Handbuch der Pflanzenanalyse", Springer 1932, 1st part, p 866–873, these fructans are obtained from aqueous extracts of suitable plant organs, after purification with precipitation agents such as e.g. lead salts, by subsequent reprecipitation which is repeated several times with organic solvents such as methanol, ethanol or acetone. The Austrian Patent specification cited above substitutes the use of toxic heavy metal salts by precipitation with the said solvents in an acid environment at pH values of 1.0 to 3.0. In this process partial degradation of the readily hydrolyzable fructan chains, lowering of the average molecular weight and loss in yield can occur. Furthermore, in all these previously known processes extensive safety measures are necessary because of inflammability and danger of explosion and undesired solvent residues may be present in the product.

Thus, it is the object of the present invention to provide a process for the isolation of fructans in which no organic solvents or toxic heavy metals have to be used and in which an improvement in yield is obtained. Moreover, the process should also ensure that pyrogens are separated so that contaminated and infected raw material can also be used.

This object is achieved according to the present invention by a process for the production of a readily water-soluble and pyrogen-free fructan which is characterized in that an aqueous extract, which is obtained in a well-known way from parts of plants containing fructan, is subjected to ultrafiltration on a first membrane which retains polymolecular carbohydrates and proteins, pyrogens as well as, if desired, other extract substances but which still allows fructan to pass through. A second ultrafiltration is carried out using the ultrafiltrate obtained in this manner on a membrane which now retains fructan but allows passage of salts, monosaccharides and low oligosaccharides. The fructan obtained in this way is free of pyrogens and organic solvents. The retentate of the second ultrafiltration according to the present invention in which the fructan is present can be processed further to directly form the renal diagnostic agent or it can also be further purified and isolated in a well-known manner. It is expedient to carry this out by drying the solution with or without previous purification on ion exchangers.

Those membranes are preferably used for the first ultrafiltration in the process according to the present invention which have an exclusion limit of 30000 to 100000 Dalton, in particular of 30000 to 50000 Dalton. Proteins, pyrogens and polymolecular polysaccharides are effectively retained by such membranes. The filtrate completely contains the extracted fructan together with low-molecular accompanying substances. Those membranes are used for the second ultrafiltration according to the present invention which have an exclusion limit of 800 to 2000 Dalton, especially of 1000 to 1500 Dalton. The fructan to be isolated is retained by such membranes but undesired low-molecular substances such as salts, monomeric and oligomeric carbohydrates are removed with the filtrate. The substantially purified fructan is then present in the retentate in a good yield, if desired, after a diafiltration with replenishment of water. The product can subsequently be purified further in a well-known manner by an additional decolorizing and/or desalting step.

Suitable ultrafiltration membranes are e.g. tube membrane FP 100 from the Paterson Company, Candy, England for the first membrane and spiral membranes Desal GE 4026F from the Desalination Systems Company, Calif., USA for the second membrane.

The pure fructan solution isolated in this way can then be directly adjusted to the desired concentration and dispensed into sterilizable containers such as ampoules and infusion bottles or dried carefully and stored for further use. Lyophilization, vacuum drying or spray drying are suitable methods of careful drying for the process according to the present invention.

The present invention also concerns a renal diagnostic agent which contains at least one fructan produced according to the present invention together with an osmotically active physiologically tolerated buffer substance. The pH of the buffer is between 5.0 and 7.0 and preferably between 6.0 and 6.5 and is present in such an amount in the renal diagnostic agent that an osmolality of 250 to 350, in particular between 280 and 320 mOsmol/kg $H_2O$ corresponding to blood isotonicity is obtained.

According to the present invention mixtures of weak acids, in particular of weak organic acids as well as alkali or earth alkali salts thereof are used as the physiologically tolerated buffer substances. Preferred acids are acetic acid and lactic acid and their sodium salts. It is also possible according to the present invention to use mixtures of weak bases, in particular organic bases and their salts, preferably their hydrochloride salts, as the tolerated buffer substances. Preferred bases are triethanolamine and basic amino acids.

In contrast to preparations of the state of the art which usually consist of sterilized aqueous solutions of inulin or water-soluble fructans without further additions (e.g. 10 g inulin per 100 ml or 25 g sinistrin per 100 ml) the renal diagnostic agent according to the present invention has an exceptionally good tolerance and storage stability.

In the renal diagnostic agents of the state of the art there is a risk of pain and haemolysis when the preparation is administered too rapidly. In addition, it has turned out that the pH value decreases in such systems during heat sterilization and longer storage in a warm environment which leads to a substantial degradation of the fructans.

The invention is elucidated further by the following examples.

EXAMPLE 1

Production of Fructan from Garlic (sinistrin)

10 kg of a commercial dried garlic granulate was stirred constantly with a solution of 10 g sodium sulfite in 30 l desalted water and left to swell for 24 hours in a closed container. The mass was extracted in a percolator with desalted water at a flow rate of 4 l/h until 100 l filtrate was present. This was filtered over an ultrafiltration coil module 1 with an exclusion limit of 50000 Dalton and the filtrate was again immediately applied to an ultrafiltration coil module 2 having an exclusion limit of 1000 Dalton via an intermediate container. After the whole extract had been applied to module 1, it was rewashed with ca. 5 l water and the retentate from module 1 was discarded. The retentate from module 2 was subjected to diafiltration while continuously replacing the filtrate volume with desalted water until the conductivity in the filtrate was less than 200 µS/cm. All filtrates from module 2 which contain salts, monomeric and oligomeric carbohydrates and other low-molecular substances were discarded. The retentate consisted of 55 kg of an already very pure solution containing 7.4% fructan corresponding to 4.07 kg dry weight. 50 g active charcoal were stirred into this in order to further purify it of traces of odorous substances and dyes and after a reaction time of 1 hour it was filtered over filter layers while re-washing in order to separate the charcoal. The colorless and odorless filtrate was evaporated in a vacuum until it had a syrup-like consistency and was dried in tanks in a vacuum oven at 80° C. to a white, blistered material.

Yield after grinding and dispensing 3.95 kg Specific rotation/alpha/20/D=−39.0° (c=10; $H_2O$) Molecular weight Mw (gel permeation chromatography)=3650

When tested on rabbits according to Pharm. Eur. the substance proved to be free of pyrogens.

EXAMPLE 2

Production of Fructan from Red Squill (sinistrin)

10 kg of commercial dried red squill was coarsely ground and extracted and twice ultrafiltered as described in example 1. The retentate consisted of 49 kg of a weakly red-colored solution containing 9.0% fructan corresponding to 4.41 kg dry weight.

For the further purification the solution was applied to a mixed-bed exchanger system consisting of 200 ml of a strongly acidic cation exchanger in the $H^+$ form and 200 ml of a moderately strong basic anion exchanger in the $OH^-$ form. The solution which was now completely colorless was dried as in example 1 after evaporation in a vacuum.

Yield after grinding and dispensing 4.2 kg Specific rotation/alpha/20/D=−39.5° (c=10; $H_2O$) Molecular weight Mw (gel permeation chromatography)=3820

When tested on rabbits according to Pharm. Eur. the substance proved to be free of pyrogens.

EXAMPLE 3

Production of an Isotonic Lactate-Buffered Renal Diagnostic Agent for Parenteral Application 13.4 g 50% sodium lactate solution DAB 9 was mixed with 700 ml dist. water for injection, 250 g fructan from garlic obtained according to example 1 was stirred into this until it completely dissolved and the pH value was adjusted to 6.30 by addition of 6.8 ml 0.1 n sodium hydroxide solution.

It was finally made up to 1 l with distilled water.

The solution was sterilized by filtering it over a 0.2µ membrane filter and 20 ml aliquots were dispensed into ampoules which were sealed and sterilized for 8 min. at 121° C. A colorless, pyrogen-free, sterile solution was obtained which was tolerated without reaction and pain when intravenously injected into humans and animals and which fulfilled all quality requirements.

Osmolality (freezing point method): 311 mOsmol/kg $H_2O$

EXAMPLE 4

Production of an Isotonic Acetate-Buffered Renal Diagnostic Agent for Parenteral Application 8.0 g sodium acetate trihydrate was mixed with 700 ml distilled water for injection, 250 g fructan from squill obtained according to example 2 was stirred into this until it completely dissolved and the pH value was adjusted to 6.30 by addition of 2.0 ml 1 m sodium hydroxide solution.

It was finally made up to 1 l with distilled water.

The solution was sterilized by filtering it over a 0.2µ membrane filter and 20 ml aliquots were dispensed into ampoules which were sealed and sterilized for 8 min. at 121° C. A colorless, pyrogen-free, sterile solution was obtained which was tolerated without reaction and pain when intravenously injected into humans and animals and which fulfilled all quality requirements.

Osmolality (freezing point method): 303 mOsmol/kg $H_2O$

It will be understood that the specification and examples are illustrative but not limitative of the present invention and that other embodiments within the spirit and scope of the invention will suggest themselves to those skilled in the art.

I claim:

1. A process for producing a pyrogen free, readily water soluble fructan, comprising:

(i) extracting a fructan containing storage organ of Liliaceae, Amaryllidaceae, or Gramineae plant with water to obtain an aqueous extract which comprises fructan;

(ii) ultrafiltering said aqueous extract on a first membrane with a molecular exclusion limit of 30000 to 100000 Daltons to separate polymolecular carbohydrates and proteins from said aqueous extract; and (iii) ultrafiltering the aqueous extract produced in step (ii) on a second membrane which has a molecular exclusion limit of 800 to 2000 Daltons to obtain a fructan retentate separated from salts, monosaccharides, and low oligosaccharides.

2. The process of claim 1, wherein said first membrane has a molecular exclusion limit between 30,000 and 100,000 Daltons.

3. The process of claim 2, wherein said first membrane has a molecular exclusion limit between 30,000 and 50,000 Daltons.

4. The process of claim 1, wherein said second membrane has a molecular exclusion limit between 800 and 2000 Daltons.

5. The process of claim 4, wherein said membrane has a molecular exclusion limit between 1000 and 1500 Daltons.

6. The process of claim 1, further comprising purifying said fructan retentate via charcoal or an ion exchanger.

7. The process of claim 1, further comprising drying said fructan retentate.

8. The process of claim 1, wherein said fructan is sinistrin.

* * * * *